United States Patent
Danérol et al.

(10) Patent No.: US 11,603,463 B2
(45) Date of Patent: Mar. 14, 2023

(54) COMPOSITION HAVING EXCELLENT PERMEABILITY TO WATER VAPOUR

(71) Applicant: URGO RECHERCHE INNOVATION ET DEVELOPPEMENT, Chenove (FR)

(72) Inventors: Anne-Sophie Danérol, Dijon (FR); Christelle Guillamaud, Chenove (FR); Jean-Marc Pernot, Dijon (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 71 days.

(21) Appl. No.: 16/768,928

(22) PCT Filed: Feb. 20, 2019

(86) PCT No.: PCT/FR2019/050385
§ 371 (c)(1),
(2) Date: Jun. 2, 2020

(87) PCT Pub. No.: WO2019/162612
PCT Pub. Date: Aug. 29, 2019

(65) Prior Publication Data
US 2021/0221997 A1 Jul. 22, 2021

(30) Foreign Application Priority Data
Feb. 20, 2018 (FR) .................. 18 51442

(51) Int. Cl.
| | | |
|---|---|---|
| *C08L 53/02* | (2006.01) | |
| *A61F 13/02* | (2006.01) | |
| *A61L 15/24* | (2006.01) | |
| *A61L 15/42* | (2006.01) | |
| *A61L 15/44* | (2006.01) | |
| *C08K 5/00* | (2006.01) | |
| *C08L 33/02* | (2006.01) | |

(52) U.S. Cl.
CPC ........ *C08L 53/025* (2013.01); *A61F 13/0213* (2013.01); *A61L 15/24* (2013.01); *A61L 15/425* (2013.01); *A61L 15/44* (2013.01); *C08K 5/0016* (2013.01); *C08L 33/02* (2013.01); *C08L 2312/00* (2013.01)

(58) Field of Classification Search
CPC .... C08L 53/025; C08L 33/02; C08L 2312/00; A61F 13/0213; A61L 15/24; A61L 15/425; A61L 15/44; C08K 5/0016
See application file for complete search history.

(56) References Cited

U.S. PATENT DOCUMENTS

| | | | |
|---|---|---|---|
| 6,080,797 A | 6/2000 | Nishida | |
| 6,270,794 B1 | 8/2001 | Cilento et al. | |
| 8,658,278 B2 * | 2/2014 | Okawara | C08L 23/0876 428/323 |
| 2003/0134552 A1 | 7/2003 | Mehawej et al. | |
| 2015/0368498 A1 * | 12/2015 | Okuyama | B32B 27/18 428/447 |

FOREIGN PATENT DOCUMENTS

| | | | | |
|---|---|---|---|---|
| CN | 1142240 A | * | 2/1997 | .......... C09D 175/04 |
| EP | 0640115 B1 | | 7/1998 | |
| WO | 2008074333 A1 | | 6/2008 | |
| WO | 2011135256 A1 | | 11/2011 | |

OTHER PUBLICATIONS

International Search Report dated Jun. 21, 2019 in corresponding International application No. PCT/FR2019/050385; 14 pages.

* cited by examiner

*Primary Examiner* — Abigail Vanhorn
(74) *Attorney, Agent, or Firm* — Maier & Maier, PLLC

(57) ABSTRACT

A novel composition including at least one styrene-block copolymer, at least one plasticiser, and particles of a cross-linked polymer having a carboxylate-group density between 2.0 and 12.0 meq/g and an average pore size between 0.005 and 1.0 μm, usable in particular for creating an elastomer matrix suitable for any device of the type device for medical aims such as a patch, a film, a strip or a dressing, preferably a dressing, intended to be applied onto the skin or suitable for any device of the functional textile type such as a sports item.

15 Claims, No Drawings

COMPOSITION HAVING EXCELLENT PERMEABILITY TO WATER VAPOUR

FIELD

The present invention relates to a novel composition comprising at least one styrene-block copolymer, at least one plasticiser, and particles of a cross-linked polymer having a carboxylate-group density between 2.0 and 12.0 meq/g and an average pore size between 0.005 and 1.0 µm, usable in particular for creating an elastomer matrix suitable for any device, for example for medical aims such as a patch, a film, a strip or a dressing, preferably a dressing, or suitable for any device of the functional textile type such as a sports item.

The present invention relates particularly to a composition having excellent permeability to water vapour. This composition is in particular capable of implementing this excellent property in such varied technical fields as the medical field, agri-food packaging, motor vehicles, sports or leisure technical items or the textile field.

BACKGROUND

A dressing can be likened in particular to a protective device allowing to cover a wound. A dressing can have a plurality of other functions that can be combined with each other or not, such as:
  protecting the wound and insulating it from the outside environment;
  allowing better healing by maintaining a favourable humid environment on the bed of the wound;
  stopping negligible bleeding;
  bringing the edges of a wound closer together;
  absorbing and managing the exudates in order to preserve the edges of the wound and the perilesional skin.

The natural healing of a wound occurs in three successive phases, each of these phases being characterised by specific and different cellular activities: the cleaning phase, the granulation phase and the epithelialisation phase. Throughout the healing process, the wound produces fluid or viscous exudates that must if possible be absorbed by a dressing or evacuated by the latter to be guided towards a reservoir outside of the wound (case of negative-pressure therapy).

According to the seriousness of the wound, the healing process can last from several days to several months. In the case of particularly exudative wounds, the fluid or viscous exudates can flood the bed of the wound and form an environment favourable to the degradation of the perilesional healthy tissue, because of the maceration of the tissue or its superinfection.

For this type of wound, the role of a dressing is therefore to absorb or to manage these fluid exudates to limit the maceration, while remaining in contact with the wound throughout the healing process, in order to guarantee a protection of the wound with respect to the outside environment.

The creation of a dressing must thus comply with complex technical specifications and reconcile contradictory characteristics. In particular, the dressing must have good breathability while avoiding the risks of leaks and of maceration, be impermeable to liquids and to bacteria while being breathable (that is to say permeable to water vapour), retain its cohesion when it is removed, and be easy to manufacture. The dressing must also be easy to place and remain in place as long as possible over time without altering the perilesional skin, have a high capacity for absorption of the exudates, and not alter the healing of the wound during its removal. Finally, the dressing must be compatible with the complementary use of a maintaining system such as a strip.

To favour a part of the management of the fluids through the dressing, it is known to implement in the latter various layers that can in particular consist of polymer materials and having high permeability to water vapour (MVTR). Indeed it is estimated that over a day, the perspiration of the skin generates an imperceptible loss of water of approximately 250 g/m$^2$ [B. Gabard in the Encyclopedic medico-chirurgicale, 50-140-E-10]. Thus, to be considered to be effective, a medical device overall must thus have a permeability to water vapour (MVTR) higher than this value.

It is thus always sought to optimise the permeability to water vapour of each of the layers forming a dressing. In particular, the development of the breathability of the elastomer matrix (also called elastomer mass), generally forming a layer of intermediate contact with the skin, takes on a particular interest. Nevertheless, the improvement of the breathability of the elastomer matrix is generally accompanied by a very significant reduction in the adhesive power of said matrix on the skin. Indeed, to promote the permeability to water vapour, it is routine to perforate the matrix, which limits the contact surface thereof with the skin, thus reducing its adhesive power.

The application WO 2008074333 from the company Coloplast describes improving the permeability of elastomer masses and describes an adhesive matrix for a medical device comprising a triblock elastomer of the S-I-S type and a water-soluble salt in order to increase the permeability to water vapour to levels of 20 g/m$^2$/24 h.

Nevertheless, compositions are still sought for elastomer matrices entering into the makeup of any device, and in particular any device for medical aims, which have improved properties of permeability to water vapour, while preserving sufficient adhesive power.

The present invention proposes a composition, in particular capable of being implemented in the form of an elastomer matrix, allowing to solve all of these issues, as well as a medical device implementing it.

SUMMARY

Thus, the present invention has allowed to develop a specific composition containing styrene-block copolymers, at least one plasticiser and particles of a cross-linked polymer having a carboxylate-group density between 2.0 and 12.0 meq/g and an average pore size between 0.005 and 1.0 µm, allowing the preparation of an elastomer matrix capable of being implemented in a device, preferably a medical device such as a dressing, said matrix having a very good permeability to water vapour (MVTR), while preserving a sufficient adhesive power (AP).

More precisely, it has been discovered, and this forms the foundation of the present invention, that by combining, in a composition, at least one styrene-block copolymer, a plasticiser, and specific particles of a cross-linked polymer having a particular carboxylate-group density and a pore size that is also particular, it is possible, in a completely surprising manner, to optimise the diffusion of water vapour through the composition, in particular when the latter is implemented in the form of an elastomer matrix. The improvement of the properties of permeability to water vapour of the composition allows, when it is implemented in a medical device such as a dressing, to optimise the level of humidity at the skin, thus favouring better healing. Thus according to a first aspect, the object of the present invention is a composition, in particular useful for the manufacturing of dressings, comprising:
- for 100 parts by weight of at least one styrene-block copolymer,
- from 12.5 to 8,000 parts by weight of at least one plasticiser,
- from 25 to 4,000 parts by weight of particles of a cross-linked polymer having a carboxylate-group density between 2.0 and 12.0 meq/g and an average pore size between 0.005 and 1.0 µm.

DETAILED DESCRIPTION

Styrene-Block Copolymer

The composition according to the invention comprises at least one styrene-block copolymer, preferably triblock of the styrene-saturated olefin-styrene type.

Triblock copolymers consisting of a combination of polystyrene blocks and of polyolefin blocks of the type polystyrene-b-poly(ethylene-butylene)-b-polystyrene (S-EB-S), or polystyrene-b-poly(ethylene-propylene)-b-polystyrene (S-EP-S), or polystyrene-b-poly(ethylene-ethylene/propylene)-b-polystyrene (S-EEP-S) having a high or ultra-high molecular weight, poly(styrene-isoprene-styrene) (SIS) or poly(styrene-isobutylene-styrene) (SIBS) are preferably used.

Alternatively, one of these triblock elastomers can be replaced with a diblock elastomer also consisting of a combination of polystyrene blocks and of polyolefin blocks, under the condition that this elastomer has similar properties in terms of molecular weight to the triblock elastomer for which it has been substituted.

Advantageously, the following is used:
- polystyrene-b-poly(ethylene-butylene)-b-polystyrene hydrogenated triblock copolymers (S-EB-S, for example KRATON® G 1651 EU, KRATON® G 1650 E or KRATON® G 1654 ES from Kraton Polymers),
- polystyrene-b-poly(ethylene-propylene)-b-polystyrene hydrogenated triblock copolymers (S-EP-S, for example KRATON® G 1701 or G 1702 from Kraton Polymers),
- polystyrene-b-poly(ethylene-ethylene/propylene)-b-polystyrene hydrogenated triblock copolymers (S-EEP-S, such as SEPTON® 4055, 4077 or 4099 from Kuraray),
- poly(styrene-isoprene-styrene) triblock copolymers and in particular a poly(styrene-isoprene-styrene) triblock copolymer in a mixture with a styrene-isoprene diblock copolymer (SIS/SI, such as VECTOR®4114A from TSRC),
- poly(styrene-isobutylene-styrene) triblock copolymers (SIBS such as SIBSTAR™ 073T and 103T from Kaneka),
- or a mixture thereof.

Nevertheless, according to an alternative embodiment, the composition according to the invention can preferably comprise a mixture of at least two triblock elastomers of the S-EB-S or S-EP-S type, regardless of the molecular weight of each of these at least two elastomers. Thus, for example, the composition according to the invention can comprise an elastomer of the KRATON® G 1650 E type and a KRATON® G 1654 ES.

According to another specific embodiment, the composition according to the invention can preferably comprise a mixture of at least two triblock elastomers of the S-EB-S or S-EP-S type, in particular of the S-EEP-S type, one of the two elastomers having a molecular weight greater than or equal to 200,000 daltons, preferably greater than or equal to 230,000 daltons and less than or equal to 350,000 daltons as measured by gel permeation chromatography, and the other elastomer having a molecular weight greater than or equal to 320,000 daltons and less than or equal to 450,000 daltons as measured by gel permeation chromatography. According to a preferred embodiment, a mixture of at least two triblock elastomers of the S-EB-S or S-EP-S type, and in particular of the S-EEP-S type, is chosen, one of the two elastomers having a molecular weight greater than or equal to 240,000 daltons and less than or equal to 310,000 daltons as measured by gel permeation chromatography, and the other elastomer having a molecular weight greater than or equal to 320,000 daltons and less than or equal to 400,000 daltons as measured by gel permeation chromatography.

Even more advantageously, again according to this specific embodiment, each elastomer has a Brookfield viscosity of at least 5000 mPa·s (in solution at 10% by weight in toluene at 30° C.).

In the context of the present embodiment described, the molecular weight designates the weight average molecular weight.

The weight average molecular weight of each elastomer (Mw) is determined according to the same method as that disclosed in the patent EP 0 640 115. Thus this determination is carried out by gel permeation chromatography (GPC) under the following conditions:
Solvent: THF for HPLC
Flow speed: 1.33 ml/min Temperature: ambient
Volume injected: 200 microlitres
Concentration of the sample: 0.05%
International standard: phenyl-hexane
Detector: Differential refractive index detector Columns, two in number, of 60 cm from Polymer Labs., mixed gel 10 microns.
Use of the data: Calibration software from Polymer labs.

The samples (100 mg) are carefully weighed and dissolved in 40 ml of THF in 50 ml round-bottom flasks. Then, 50 microlitres of marker are added when the polymer is dissolved and the solutions are completed up to the 50 ml mark. Then, they are filtered through a 0.2 µM pressure filter and they are injected into the GPC. 4 separate solutions of various mixtures of polystyrene standards are prepared in calibrated glass vials and a known volume of marker is added thereto.

The marker is used to correct the variations in flow. The software creates a calibration curve on the basis of the mixtures of standards by using a polynomial adjustment of the third order.

The values obtained for various elastomers are listed in the following table:

| Elastomer | Molecular weight (Mw) |
|---|---|
| Septon ®4055 | 308,000 daltons |
| Septon ®4077 | 392,000 daltons |
| Septon ®4155 | 290,000 daltons |
| Septon ®2005 | 257,000 daltons |
| Septon ®2006 | 251,000 daltons |
| Septon ®2105 | 275,000 daltons |
| Septon ®2055 | 250,000 daltons |
| Kraton ®G 1651 EU | 240,000 daltons |

Thus, a composition comprising a combination of an elastomer of the Kraton® brand such as Kraton® G 1651 EU or of another copolymer of the Kraton® brand from the G series having the desired molecular weight property with an elastomer of the Septon® brand such as Septon® 4077 or Septon® 4099 is envisaged by this specific embodiment of the invention.

Likewise, a matrix comprising a combination of a copolymer of the Septon® brand such as Septon®4055 or of another copolymer of the Septon® brand listed in the table above or of any given copolymer of the Septon brand having the properties mentioned above and not listed in the table above with another copolymer of the Septon® brand such as Septon® 4077 or Septon® 4099 is envisaged by this specific embodiment of the invention.

According to a preferred embodiment of the invention, the 100 parts by weight of styrene-block copolymer represent 1 to 40% by weight of the composition, preferably 3 to 30% by weight.

According to a first more preferred embodiment, when the styrene-block copolymer consists of a combination of polystyrene blocks and of polyolefin blocks of the type polystyrene-b-poly(ethylene-butylene)-b-polystyrene (S-EB-S), or polystyrene-b-poly(ethylene-propylene)-b-polystyrene (S-EP-S), or polystyrene-b-poly(ethylene-ethylene/propylene)-b-polystyrene (S-EEP-S) having a high or ultra-high molecular weight, the 100 parts by weight of styrene-block copolymer represent 1 to 20% by weight of the composition, preferably 3 to 10% by weight.

According to a second more preferred embodiment, when the styrene-block copolymer consists of a combination of polystyrene blocks and of polyolefin blocks of the type poly(styrene-isoprene-styrene) (SIS) or poly(styrene-isobutylene-styrene) (SIBS), the 100 parts by weight of styrene-block copolymer represent 10 to 40% by weight of the composition, preferably 10 to 30% by weight.

Particles of Cross-Linked Polymer

The compositions according to the invention comprise particles of a cross-linked polymer having a carboxylate-group density between 2.0 and 12.0 meq/g and an average pore size between 0.005 and 1.0 µm.

The "average size of the pores" designates an average size expressed in volume, the value of which can be calculated by the formula 4V/S where S is the specific surface area and V is the volume of pores per unit of mass obtained from a pore-size distribution measured by the mercury compression method.

The average size of the pores, expressed in volume, can be determined by any method known to a person skilled in the art, for example by mercury intrusion porosimetry or nitrogen adsorption sorptometry.

For example, the nitrogen adsorption sorptometry can be carried out via a Micromeritics TriStar II apparatus coupled with a Micromeritics Smart VacPrep. The batch to be characterised is for example subjected to a degassing phase for 24 hours at ambient temperature then 5 hours at 50° C. The temperature during the test is −196° C., and the pressure is maintained in a range of 0<P/P0<0.30 with P0=saturation vapour pressure of the nitrogen.

The mercury intrusion porosimetry can be implemented via a measurement cell for powder having a volume of 3 cm3 and a capillary having a volume of 0.387 cm3. The analysis is carried out in two steps: in a first step the "penetrometer-sample" assembly is in a "low pressure" configuration (measurement from 0.52 psia (primary vacuum) up to 30 psia or 2 bar); in a second step the "penetrometer-sample" assembly is in a "high pressure" configuration (measurement up to 6,000 psia or 4,000 bar). The minimum size of the accessible pores is 3 mm.

According to a preferred embodiment, the particles of cross-linked polymer implemented in the context of the present application have a specific surface area of less than 1 m$^2$/g. The specific surface area can in particular be measured by the physical adsorption BET method, well known to a person skilled in the art.

According to a preferred embodiment, the polymer implemented is an organic polymer.

The polymer implemented has a carboxylate-group density between 2.0 and 12.0 meq/g. The carboxylate group is a polar group conferring the desired properties of absorption of humidity onto the polymer.

There is no particular limitation as to the nature of the salt implemented for the formation of the carboxylate groups. This can for example be a salt of an alkali metal such as Li, Na, K, Rb and Cs, an alkaline earth metal such as Be, Mg, Ca, Sr and Ba, other metals such as Cu, Zn, Al, Mn, Ag, Fe, Co and Ni, NH4 and organic cations such as amines.

Preferably, the carboxylate salt used in the context of the present invention is sodium carboxylate.

The introduction of carboxylate groups can be carried out by any method known to a person skilled in the art. For example, a monomer carrying a carboxylate group can be homopolymerised or copolymerised with other monomers to give the polymer according to the invention. Alternatively, a polymer carrying carboxylate groups can be salified. Again alternatively, a polymer can first be grafted by carboxylate groups, which are then salified. These methods for introducing carboxylate groups are described in detail in the patent application U.S. Pat. No. 6,080,797 which is reused and incorporated by reference into the present application.

A typical example of particles of cross-linked polymer according to the invention can be created from acrylonitrile or methacrylic acid.

More particularly, microparticles of cross-linked polymer, in particular of polyacrylonitrile, according to the invention can be obtained by coagulation or by precipitation polymerisation to give an agglomerate of particles of polyacrylonitrile or a polymer of acrylonitrile, this agglomerate or this polymer undergoes a cross-linking with hydrazine or a derivative of hydrazine and finally an at least partial hydrolysis of the residual nitrile groups so as to obtain a carboxylate-group density between 2.0 and 12.0 meq/g. Moreover, the various steps of this method allow to obtain an average pore size between 0.005 and 1.0 µm.

For illustrative purposes, a first method allowing the manufacturing of a cross-linked polymer according to the invention involves preparing a solution of polymer from an acrylonitrile polymer and a solvent, then coagulating said solution in a solvent (which is not a solvent for said acrylonitrile polymer) to obtain a porous acrylonitrile polymer, then cross-linking said porous polyacrylonitrile with a hydrazine, said cross-linking being finally followed by a hydrolysis of the residual nitrile groups in such a way as to obtain a carboxylate-group density between 2.0 and 12.0 meq/g and an average pore size between 0.005 and 1.0 µm.

Alternatively, a second method allowing the manufacturing of a cross-linked polymer according to the invention involves precipitation polymerising a mixture of monomers containing at least 50% by weight of acrylonitrile to obtain a porous acrylonitrile polymer, then cross-linking of said porous polyacrylonitrile with a hydrazine and hydrolysis of the residual nitrile groups in such a way as to obtain a carboxylate-group density between 2.0 and 12.0 meq/g and an average pore size between 0.005 and 1.0 µm.

These methods are described more precisely in the patent application U.S. Pat. No. 6,080,797 which is reused and incorporated by reference into the present application.

Nevertheless, any particles having the required properties of carboxylate-group density or pore size are suitable for the creation of a composition according to the invention. A typical alternative would promote for example the creation of such particles from methacrylic acid as described in example 5 of the patent U.S. Pat. No. 6,080,797.

There is no particular limitation as to the shape of the particles of polymer implemented according to the invention.

In the sense of the present invention, the cross-linked polymer according to the invention is characterised by an equilibrium relative humidity (measured at 20° C. under at atmosphere at 65% relative humidity) between 20 and 80%, preferably between 30 and 70%.

According to a specific embodiment, the particles of cross-linked polymer according to the invention have an average size between 0.1 and 100 µm, preferably between 0.3 and 64 µm.

According to another specific embodiment, the particles of a cross-linked polymer according to the invention have an apparent density between 0.1 and 1 $g/cm^3$, preferably between 0.2 and 0.7 $g/cm^3$.

Such particles are for example marketed by the company Japan Exlan Co., Ltd under the name of TAFTIC® HU 720SF or TAFTIC® HU 1200P.

They can be introduced into the compositions according to the invention in the form of powder, or in the form of particles in suspension or in dispersion in water.

The composition according to the invention comprises between 25 and 4,000 parts by weight, for 100 parts by weight of at least one styrene-block copolymer, of a cross-linked polymer having a carboxylate-group density between 2.0 and 12.0 meq/g and an average pore size between 0.005 and 1.0 µm, preferably from 30 to 3,000 parts by weight, and more preferably from 35 to 2,000 parts by weight.

The Plasticiser

The composition according to the invention comprises at least one (or more) plasticiser compound(s).

The plasticisers capable of being used are well known and intended to improve the properties of stretching, flexibility, extrudability or implementation of the copolymers. For this purpose one or more plasticisers if necessary can be used.

In general, liquid compounds, compatible with the saturated olefin central sequence of the aforementioned sequenced copolymers, are preferred as plasticisers.

Among the plasticiser compounds capable of being used for this purpose, the plasticising mineral oils are in particular mentioned.

Alternatively, synthetic products containing liquid mixtures of saturated hydrocarbons for example such as the products marketed by the company TOTAL under the name GEMSEAL® and in particular the product GEMSEAL® 60 which is an isoparaffinic mixture coming from a totally hydrogenated petroleum cut can also be used.

In the context of the present invention, plasticising oils and in particular mineral oils formed by compounds of a paraffinic or naphthenic nature, or by their mixtures, in variable proportions, are preferably used.

Particularly preferred plasticising mineral oils are formed by mixtures of compounds of a paraffinic and naphthenic nature.

Among the particularly suitable plasticising oils, mention can be made of the products marketed by the company SHELL under the names ONDINA® and in particular ONDINA® 919 or 933, or the oil marketed by the company PETRO CANADA under the product name PURETOL® 9D or the oils BLANDOL® or KAYDOL® marketed by Sonneborn or the oils PIONIER® 2076P or 2071N marketed by Hansen & Rosenthal.

Mention can also be made of the products marketed by Croda under the name CRODAMOL™ DOA (Diethylhexyl adipate) or marketed by Eigenmann & Veronelli under the brand name LINCOL DOA-C (Diethylhexyl adipate).

Other than the oils, the plasticiser can comprise VASELINE® (petroleum jelly). The petroleum jelly implemented in the compositions of the invention is a commercially available petroleum jelly compliant with the French Pharmacopeia.

In the context of the present invention, the petroleum jelly is present in a quantity of 2.5 to 3,000 parts by weight, preferably 12.5 to 2,500 parts by weight, for 100 parts by weight of at least one styrene-block copolymer.

According to an alternative of the present invention, a mineral oil combined with a small quantity of vegetable oil can also be used.

In the context of the present invention, the plasticiser is present in a quantity of 12.5 to 8,000 parts by weight, preferably 375 to 6,500 parts by weight for 100 parts by weight of at least one styrene-block copolymer.

The Tackifying Resins

The composition according to the invention can also comprise at least one tackifying resin.

Among the tackifying resins capable of being used according to the invention, mention can be made of the modified polyterpene or terpene resins, the rosin resins, the hydrocarbon resins, the mixtures of cyclic, aromatic and aliphatic resins, or mixtures of these resins.

Such products are marketed for example:
  by the company ARAKAWA Chemical Industries under the name ARKON®P which are hydrogenated polycyclopentadiene resins;
  by the company EXXON Chemical under the name ESCOREZ™ and in particular the series of the 5000 resins which are hydrogenated;
  by the company CRAY VALLEY under the name WINGTACK®, and in particular WINGTACK® 86 which is a synthetic resin formed by C5/C9 copolymers or WINGTACK® 10 which is a resin containing synthetic polyterpene;
  by the company EASTMAN under the name KRISTALEX® and in particular KRISTALEX 3105SD and F100, or the company ARIZONA CHEMICAL under the name SYLVARES™ SA100 which is a resin containing alpha-methylstyrene,
  by the company Kolon Industries under the name SUKOREZ® of grades SU-90; SU-100; SU-100S.

In general, in order to avoid the problems of colouration and of stability of the unsaturated resins, the use of hydrogenated resins is preferred, in particular with the triblock copolymers with a saturated central sequence since said resins are much more compatible with the latter that the unsaturated resins of the WINGTACK® type that are used substantially with triblock copolymers with an unsaturated central sequence.

The tackifying resins can be used alone or in a mixture with other tackifying products, preferably in a proportion of 50 to 7,000 parts by weight for 100 parts by weight of at least one styrene-block copolymer and more particularly of 75 to 6,000 parts by weight.

The Hydrocolloids and Other Absorbent Particles

According to one embodiment of the invention, the compositions according to the invention comprise hydrophilic particles of a hydrocolloid (or particles of hydrocolloid).

These particles indeed allow the painless removal of an interface dressing and the maintaining of a humid environment at the wound in order to promote healing.

For this purpose, a small quantity of hydrophilic particles of a hydrocolloid is thus either disposed on the surface of the elastomer matrix once the latter has been formed or is, preferably, dispersed homogenously in the composition according to the invention.

Here, "hydrocolloid" or "particles of hydrocolloid" is intended to designate any compound usually used by a person skilled in the art for its ability to absorb the aqueous liquids such as water, physiological serum or the exudates of a wound.

As suitable hydrocolloids, mention can be made for example of pectin, the alginates, the natural vegetable gums like in particular gum Karaya, the derivatives of cellulose such as the carboxymethyl celluloses and their salts of alkaline metal such as sodium or calcium.

Finally, as an alternative to the hydrocolloids, absorbent particles can be used. Among the latter are synthetic polymers containing salts of acrylic acids, known by the name "superabsorbents", or the products marketed by the company CIBA Specialty Chemicals under the name SALCARE® SC91. Another product of interest is that marketed under the name AQUA KEEP™ by Sumitomo, preferably the product AQUA KEEP™ 10SH-NF.

The hydrocolloids preferred in the context of the present invention are the carboxymethyl cellulose salts of alkaline metal, and in particular sodium carboxymethyl cellulose (CMC) like the marketed product BLANOSE™ 7H4XF PH by the company ASHLAND.

The size of the particles of hydrocolloid is generally between 50 and 100 microns, advantageously approximately 80 microns.

In general, the quantity of particles of hydrocolloid incorporated into the composition according to the invention is advantageously approximately 5 to 2,000 parts by weight, preferably from 12.5 to 1,800 parts by weight, and more preferably from 25 to 1,500 parts by weight, for 100 parts by weight of at least one styrene-block copolymer.

The Antioxidants

The composition according to the invention can also comprise antioxidants.

Here, "antioxidant" is intended to designate the compounds routinely used by a person skilled in the art to ensure the stability of the compounds entering into the formulation of the compositions, in particular with respect to oxygen, heat, ozone or ultraviolet radiation.

As examples of suitable antioxidants, mention can be made in particular of the phenolic antioxidants like in particular the products marketed by the company BASF under the names IRGANOX® 1010, IRGANOX® 565, IRGANOX® 1076 or the sulphurated antioxidants like for example zinc dibutyldithiocarbamate marketed by the company AKZO under the name PERKACIT®ZDBC.

In the context of the present invention, the combination of IRGANOX 1010 and of PERKACIT®ZDBC is preferred.

In general these antioxidants can be used alone or in combination in a quantity of approximately 0.125 to 200 parts by weight, preferably from 0.250 to 100 parts by weight, for 100 parts by weight of at least one styrene-block copolymer.

In the context of the present invention, the use of the product IRGANOX® 1010 in a quantity of between 0.125 and 100 parts by weight, for 100 parts by weight of at least one styrene-block copolymer, is preferred.

Additional Active Ingredients

Besides the antioxidants, the composition according to the invention can comprise one or more other active substance(s) allowing to induce or to accelerate healing or capable of playing a favourable role in skin treatment.

Among these active substances, mention can be made, in particular, as examples, of:

- the agents promoting healing such as retinol, vitamin A, vitamin E, N-acetyl hydroxyproline, the extracts of *Centella Asiatica*, papain, the essential oils of thyme, niaouli, rosemary, sage, hyaluronic acid, potassium sucrose octasulphate, sucralfate, allantoin, metformin;
- the antibacterial agents such as the salts or complexes of silver (like the sulphates of silver, the nitrates of silver, the sulphamides of silver or the zeolites containing silver), the salts of zinc or of copper, metronidazole, neomycin, the penicillins, clavulanic acid, the tetracyclines, minocycline, chlorotetracycline, the aminoglycosides, amikacin, gentamicin, the probiotics;
- the antiseptics such as chlorhexidine, trichlosan, biguanide, hexamidine, thymol, Lugol's iodine, povidone-iodine, the chloride of benzalkonium and of benzethonium;
- the analgesics such as paracetamol, codeine, dextropropoxyphene, tramadol, morphine and its derivatives, the corticoids and their derivatives;
- the local anaesthetics such as lidocaine, benzocaine, dibucaine, pramoxine hydrochloride, bupivacaine, mepivacaine, prilocaine, etidocaine;
- the anti-inflammatory drugs such as the nonsteroidal anti-inflammatory drugs (NSAIDs), aspirin or acetylsalicylic acid, ibuprofen, ketoprofen, flurbiprofen, diclofenac, aceclofenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid, mefenamic acid.

These active agents can be used in a quantity of approximately 0.025 to 2,000 parts by weight, preferably from 2.5 to 1,500 parts by weight, and more preferably from 5 to 1,000 parts by weight, for 100 parts by weight of at least one styrene-block copolymer.

Of course, the composition according to the invention can also comprise one or more other compounds known for their action in the cleaning phase for example such as:

enzymes;

urea.

Adjuvants

As adjuvants capable of being used in the compositions according to the invention, mention can be made of the compounds known for promoting the salting out of the active agents, for example like the products MONTANOX® 80 PHA Premium or SEPINOV® EMT 10 or SEPINEO™ DERM which are routinely used in the URGOTUL® products that incorporate active agents.

These adjuvants can be used in a quantity of approximately 2.5 to 1,500 parts by weight, for 100 parts by weight of at least one styrene-block copolymer.

Of course the specific embodiments that have just been described can be implemented separately or according to any one of their combinations.

Elastomer Matrix

In order to create any device, and preferably a dressing, the compositions according to the invention can be hot formed by casting, soaking, moulding or transfer to form an elastomer matrix.

The object of the invention, according to another aspect, is also an elastomer matrix obtained from a composition according to the invention as described above.

This matrix can be continuous, that is to say solid and not having any perforation, or discontinuous, that is to say having at least one perforation or through-holes. Preferably, said elastomer matrix is continuous.

The through-holes can be created by perforation or punching of a composition according to the invention previously formed into a thin layer, alone or combined with a temporary support.

Alternatively, the elastomer matrices according to the invention can be manufactured by hot casting a composition as described above onto a support etched (plate or cylinder) with the pattern selected to form through-holes, followed by cooling and removal from the mould.

The through-holes can have any given geometry and have for example a circular, rectangular, trapezoidal or square transverse cross-section.

Their surface area is generally between 1 and 7 mm$^2$.

These holes are distributed, preferably regularly, with a density such that the total surface area of the holes represents between 20 and 70% and preferably between 30 and 60% of the total surface of the dressing.

In general, the elastomer matrices according to the invention have a thickness between 0.1 μm and 5 mm, and preferably between 20 μm and 2 mm.

It is also possible to use this elastomer matrix to coat a frame or a support.

Device

The object of the invention, according to a preferred embodiment, is therefore a medical device such as a patch, a film, a strip or a dressing, or a device of the functional textile type such as a sports item. Preferably, said device is a dressing characterised in that it comprises an elastomer matrix as described above.

According to a preferred embodiment, the present application aims to cover a dressing comprising an elastomer matrix in the form of a thin layer obtained from a composition comprising:

for 100 parts by weight of at least one styrene-block copolymer, from 12.5 to 8,000 parts by weight of at least one plasticiser, from 25 to 4,000 parts by weight of particles of a cross-linked polymer having a carboxylate-group density between 2.0 and 12.0 meq/g and an average pore size between 0.005 and 1.0 μm.

The elastomer matrix can be used alone to form the device or in combination with one or more layers, such as foams, textiles, composite materials or films.

The elastomer matrix can be at any level of the device, that is to say form any one of the various layers of the device, and can be in contact with the skin, the wound.

The present invention is illustrated in the non-limiting examples presented below.

EXAMPLES

Example 1

Preparation of the Compositions

The compositions of examples 1 to 14 were made using the following components in the proportions, expressed in parts by weight, mentioned in table 1 below.

Elastomer: comprises at least one sequenced copolymer of poly(styrene-olefin-styrene) (in abbreviated form for example SEBS, SEEPS, SIS/SI or SIBS, respectively):

KRATON® G 1654 ES
KRATON® G 1650 E
KRATON® G 1651 EU
SEPTON® 4055
VECTOR® 4114A
SIBSTAR™ 103T

Plasticiser: mineral oil ONDINA® 919 or 933 marketed by the company SHELL, PIONIER® 2076P or 2071N marketed by Hansen & Rosenthal or BLANDOL® marketed by Sonneborn.

Petroleum Jelly: VASELINE CODEX® A marketed by the company AIGLON

Antioxidant: IRGANOX® 1010 marketed by the company BASF and/or PERKACIT®ZDBC by the company AKZO Hydrocolloid: CMC sodium carboxymethyl cellulose BLANOSE® 7H4XFPH marketed by the company ASHLAND, or absorbent particles AQUA KEEP™ 10SH-NF from Sumitomo Resins:

ESCOREZ™ 5380, cycloaliphatic hydrocarbon resin, having a softening point located between 80-90° C., marketed by Exxon Mobil, SUKOREZ®SU-100S, polycyclopentadiene resin having a softening point located between 97 and 106° C., marketed by Kolon Industries Particles of Cross-Linked Polymer:

TAFTIC® HU-720 SF from the company Japan Exlan Co., Ltd

TAFTIC® HU-1200 P from the company Japan Exlan Co., Ltd

Manufacturing of the Composition

In a device for hot mixing, first the plasticiser and/or the petroleum jelly are introduced at a temperature of less than 90° C., then in a second step, the copolymer(s) and the antioxidant are added to the previous mixture at a setting temperature between 160 and 180° C. In a last step, the other compounds including the hydrocolloid or the absorbent particle, the resin, as well as the particles of cross-linked polymer according to the invention are added until a homogenous mixture is obtained.

Finally, the device for hot mixing is emptied.

Measurement of the Permeability to Water Vapour:

The conditions for carrying out the test are based on the standard NF EN 13726—liquids in contact.

Equipment/Instruments

Scale resolution 0.1 mg

Hollow punch diameter 44 mm

Measurement cell made of aluminium having a diameter D=35.7 mm and surface area 10 cm$^2$ Volumetric flask (=25 mL) or metering pump Thermostatically controlled air oven at 37° C. and <20% relative humidity (RH)

Air-conditioned room at 21° C.+/−2—RH at 60%+/−15

Reactants: demineralised water and NaCl, CaCl2 solution

Sampling/Conditioning of the Samples

Number of test specimens n≥5
Temperature T=37° C.±2° C.
Hygrometry RH<20%
Operating Mode
The conditions for carrying out the test are based on the standard NF EN 13726—liquids in contact and were the following.
The principle of this measurement is the following:
1. Pour a volume V of liquid into the cell.
2. Position, on the opening of the measurement cell, the sample to be tested (adhesive face on the siliconised joint if adhesive is applied to the product).
3. Position above the sample, centred to avoid leaks, the maintaining device then screw the 3 screws until stopped.
4. Weigh the assembly→$P_{MVTR0}$.
5. Turn over the cells to place the liquid in contact with the sample. Place this assembly in an oven at a temperature T for a time t (t expressed in hours).
6. Weigh within 5 minutes of the end of the test (t) the entire device→$P_{MVTR1}$.

Expression of the Results
Calculate the Water Vapour Transmission Rate (MVTR)

$$MVTR1=(P_{MVTR0}-P_{MVTR1})/(\pi D^2/4)$$

$$MVTR1=4(P_{MVTR0}-P_{MVTR1})/\pi D^2$$

Or, under the standard conditions, $MVTR1 = (P_{MVTR0}-P_{MVTR1})/(10*10^{-4})$

Express the result in $g/m^2/24$ h.
Calculate the average of the n tests, give or take one $g/m^2$.

$$MVTR = \frac{1}{n}\sum_{i=1}^{n} MVTR_i$$

The quantities of each of the compounds introduced into each of the compositions 1 to 14 are given in parts by weight in table 1.

TABLE 1

|  | Compo 1 | Compo 2 | Compo 3 | Compo 4 | Compo 5 | Compo 6 | Compo 7 |
|---|---|---|---|---|---|---|---|
| PIONIER ® 2076P | 741 | 736 | 741 | 736 |  |  |  |
| PIONIER ® 2071N |  |  |  |  | 70 | 70 |  |
| BLANDOL ® |  |  |  |  |  |  | 70 |
| ONDINA ® 933 |  |  |  |  |  |  |  |
| VASELINE CODEX ® A |  |  |  |  |  |  |  |
| KRATON ® G 1651 EU | 100 | 100 |  |  |  |  |  |
| SEPTON ® 4055 |  |  | 100 | 100 |  |  |  |
| VECTOR ® 4114A |  |  |  |  | 100 | 100 |  |
| SIBSTAR ™ 103T |  |  |  |  |  |  | 100 |
| KRATON ® G 1650 E |  |  |  |  |  |  |  |
| KRATON ® G 1654 ES |  |  |  |  |  |  |  |
| IRGANOX ® 1010 | 4 | 5 | 4 | 5 | 1.5 | 2 | 1.5 |
| PERKACIT ® ZDB C |  |  |  |  | 1.5 | 2 | 1.5 |
| ESCOREZ ™ 5380 | 1,115 | 1,109 | 1,115 | 1,109 | 150 | 150 | 150 |
| SUKOREZ ® SU-100S |  |  |  |  |  |  |  |
| TAFTIC ® HU-1200 P |  |  |  |  |  |  |  |
| TAFTIC ® HU-720 SF |  | 488 |  | 488 |  | 80 |  |
| CMC BLANOSE ® 7H4XFPH |  |  |  |  |  |  |  |
| AQUA KEEP ™ 10SH-NF |  |  |  |  |  |  |  |

|  | Compo 8 | Compo 9 | Compo 10 | Compo 11 | Compo 12 | Compo 13 | Compo 14 |
|---|---|---|---|---|---|---|---|
| PIONIER ® 2076P |  | 741 | 732 |  |  | 780 | 774 |
| PIONIER ® 2071N |  |  |  |  | 70 |  |  |
| BLANDOL ® | 70 |  |  |  |  |  |  |
| ONDINA ® 933 |  |  |  | 70 |  |  |  |
| VASELINE CODEX ® A |  | 180 | 179 |  |  |  |  |
| KRATON ® G 1651 EU |  |  |  |  |  | 100 | 100 |
| SEPTON ® 4055 |  |  |  |  |  |  |  |
| VECTOR ® 4114A |  |  |  | 100 | 100 |  |  |
| SIBSTAR ™ 103T | 100 |  |  |  |  |  |  |
| KRATON ® G 1650 E |  |  | 32 | 32 |  |  |  |
| KRATON ® G 1654 ES |  |  | 68 | 68 |  |  |  |

TABLE 1-continued

| | | | | | | | | |
|---|---|---|---|---|---|---|---|---|
| IRGANOX ® 1010 | 2 | 2.5 | 3 | 2 | 2 | 3 | 4 | |
| PERKACIT ® ZDBC | 2 | | | 2 | 2 | | | |
| ESCOREZ ™ 5380 | 150 | | | 150 | 150 | | | |
| SUKOREZ ® SU-100S | | | | | | 729 | 722 | |
| TAFTIC ® HU-1200 P | | | | | | | 400 | |
| TAFTIC ® HU-720 SF | 80 | | 298 | | 120 | | | |
| CMC BLANOSE ® 7H4XFPH | | 180 | 179 | | | | | |
| AQUA KEEP ™ 10SH-NF | | | | 120 | | | | |

Results:

TABLE 2

| | Permeability to water vapour (MVTR at 37° C. in g/m²/24 h) | Variation in the permeability to water vapour |
|---|---|---|
| Composition 1 | 51 | +35,588% |
| Composition 2 | 18,201 | |
| Composition 3 | 48 | +38,242% |
| Composition 4 | 18,404 | |
| Composition 5 | 55 | +15,867% |
| Composition 6 | 8,782 | |
| Composition 7 | 24 | +2,817% |
| Composition 8 | 700 | |
| Composition 9 | 91 | +4,085% |
| Composition 10 | 3,808 | |
| Composition 11 | 26 | +62,950% |
| Composition 12 | 16,367 | |
| Composition 13 | 81 | +2,770% |
| Composition 14 | 2,244 | |

The addition of particles according to the invention consisting of a cross-linked polymer having a carboxylate-group density between 2.0 and 12.0 meq/g and an average pore size between 0.005 and 1.0 µm allows to drastically increase the permeability to water vapour (MVTR) of the compositions.

Example 2

Preparation of the Compositions

The following compositions 15 to 19 were made using the following components in the proportions, expressed in parts by weight, mentioned in table 3 below.

Elastomer: sequenced copolymer of poly(styrene-ethylene-butylene-styrene) (abbreviated as SEBS):
  KRATON® G 1651 EU Plasticiser: mineral oil PIONIER® 2076P marketed by Hansen & Rosenthal or BLANDOL® marketed by Sonneborn Antioxidant: IRGANOX® 1010 by the company BASF Resin:
  ESCOREZ™ 5380, cycloaliphatic hydrocarbon resin, having a softening point located between 80-90° C., marketed by Exxon Mobil, or
  SUKOREZ®SU-100S, polycyclopentadiene resin having a softening point located between 97 and 106° C., marketed by Kolon Industries Particles of Cross-Linked Polymer:
  TAFTIC® HU-720 SF from the company Japan Exlan Co., Ltd Manufacturing of the Composition In a device for hot mixing, first the plasticiser and/or the petroleum jelly are introduced at a temperature of less than 90° C., then in a second step, the copolymer(s) and the antioxidant are added to the previous mixture at a setting temperature of 160° C. Finally, in a last step, the other compounds including the hydrocolloid or the absorbent particle, the resin, as well as the particles of cross-linked polymer according to the invention are added until a homogenous mixture is obtained. Finally, the device for hot mixing is emptied.

Measurement of the Permeability to Water Vapour:

The conditions for carrying out the test are based on the standard NF EN 13726—liquids in contact.

Equipment/Instruments

Scale resolution 0.1 mg
Hollow punch diameter 44 mm
Measurement cell made of aluminium having a diameter D=35.7 mm and surface area 10 cm²
Volumetric flask (=25 mL) or metering pump
Thermostatically controlled air oven at 37° C. and <20% relative humidity (RH)
Air-conditioned room at 21° C.+/−2—RH at 60%+/−15
Reactants: demineralised water and NaCl, CaCl2 solution Sampling/Conditioning of the Samples Number of test specimens n≥5.
Temperature T=37° C.±2° C.
Hygrometry RH<20%

Operating Mode

The conditions for carrying out the test are based on the standard NF EN 13726—liquids in contact, are the following.

The principle of this measurement is the following:
7. Pour a volume V of liquid into the cell.
8. Position, on the opening of the measurement cell, the sample to be tested (adhesive face on the siliconised joint if adhesive is applied to the product).
9. Position above the sample, centred to avoid leaks, the maintaining device then screw the 3 screws until stopped.
10. Weigh the assembly→$P_{MVTR0}$.
11. Turn over the cells to place the liquid in contact with the sample. Place this assembly in an oven at a temperature T for a time t (t expressed in hours).
12. Weigh within 5 minutes of the end of the test (t) the entire device→$P_{MVTR1}$.

Expression of the Results
Calculate the water vapour transmission rate (MVTR)

$$MVTR1 = (P_{MVTR0} - P_{MVTR1})/(\pi D^2/4)$$

$$MVTR1 = 4(P_{MVTR0} - P_{MVTR1})/\pi D^2$$

Or, under the standard conditions, MVTR1=
$(P_{MVTR0} - P_{MVTR1})/(10*10^{-4})$ Express the result in g/m²/24 h.
Calculate the average of the n tests, give or take one g/m².

$$MVTR = \frac{1}{n}\sum_{i=1}^{n} MVTR_i$$

The quantities of each of the compounds introduced into the compositions 15 to 19 are given in parts by weight in table 3.

TABLE 3

|  | Compo. 15 | Compo. 16 | Compo. 17 | Compo. 18 | Compo. 19 |
|---|---|---|---|---|---|
| PIONIER ® 2076P | 739 | 739 | 739 | 738 | 741 |
| KRATON ® G1651 EU | 100 | 100 | 100 | 100 | 100 |
| IRGANOX ® 1010 | 4.5 | 4.5 | 4.5 | 4.5 | 4 |
| ESCOREZ ™ 5380 | 1,113 |  | 1,114 | 1,112 | 1,115 |
| TAFTIC ® HU-720 SF | 279 | 279 | 345 | 414 |  |
| SUKOREZ ® SU-100S |  | 1,113 |  |  |  |

Measurement of the Adhesive Power at 180°:

The first step involves placing one of the compositions 15 to 19 of example 2 onto a support of the nonwoven type and then cutting out a test specimen that is to say a strip of one of these combinations 20 mm wide and 300 mm long.

In parallel, in a second step, a strip of card stock having a width and length greater than those of the test specimen is cut out.

The test specimen is then applied, with a slight pressure of the finger on the card stock in parallel to its largest dimension, without stretching the strip and while avoiding including the slightest air bubble.

Two there-and-back movements are carried out using an applicator roll, at a speed V1=10 mm/s and a weight P=2 kg/cm, without additional pressure, to obtain close contact between the adhesive mass and the surface of the paper.

The assembly is left to climatise at a temperature of 23+/−2° C. for a time t=10 min.

Finally, in a final step, the average force F of the peeling at 180° carried out at a speed V2=300 mm/min of the test specimen on the card stock is recorded via an electronic dynamometer.

TABLE 4

|  | Permeability to water vapour (MVTR at 37° C. in g/m²/24 h) | Adhesive power at 180° on card stock (cN/cm) |
|---|---|---|
| Composition 15 | 295 +/− 40 | 88 +/− 8 |
| Composition 16 | 290 +/− 37 | 118 +/− 7 |
| Composition 17 | 2,102 +/− 431 | 94 +/− 2 |

TABLE 4-continued

|  | Permeability to water vapour (MVTR at 37° C. in g/m²/24 h) | Adhesive power at 180° on card stock (cN/cm) |
|---|---|---|
| Composition 18 | 3,048 +/− 60 | 88 +/− 7 |
| Composition 19 | 51 +/− 1 | 97 +/− 9 |

The addition of particles of a cross-linked polymer having a carboxylate-group density between 2.0 and 12.0 meq/g and an average pore size between 0.005 and 1.0 µm allows to drastically increase the permeability to water vapour of said compositions. Moreover, a dose-dependent effect of the introduction of these particles into each of the compositions of example 2 is observed, thus increasing the permeability to water vapour without deteriorating the adhesive power of said compositions.

The invention claimed is:

1. A composition comprising:
   for 100 parts by weight of at least one styrene-block copolymer,
   from 12.5 to 8,000 parts by weight of at least one plasticiser,
   from 25 to 4,000 parts by weight of particles of a cross-linked polymer having a carboxylate-group density between 2.0 and 12.0 meq/g and an average pore size between 0.005 and 1.0 µm, and the particles of the cross-linked polymer have a specific surface area of less than 1 m²/g.

2. The composition according to claim 1, wherein the styrene-block copolymer is a styrene-saturated olefin-styrene triblock.

3. The composition according to claim 2, wherein the styrene-saturated olefin-styrene triblock copolymer is selected from the group consisting of polystyrene-b-poly(ethylene-propylene)-b-polystyrene (S-EP-S), polystyrene-b-poly(ethylene-butylene)-b-polystyrene (S-EB-S), polystyrene-b-poly(ethylene-ethylene/propylene)-b-polystyrene (S-EEP-S), poly(styrene-isoprene-styrene) (SIS), poly(styrene-isobutylene-styrene) (SIBS), and mixtures thereof.

4. The composition according to claim 1, wherein the particles of cross-linked polymer have an average size between 0.1 and 100 µm.

5. The composition according to claim 4, wherein the particles of cross-linked polymer have an average size between 0.3 and 64 µm.

6. The composition according to claim 1, wherein the cross-linked polymer is prepared from acrylonitrile or methacrylic acid.

7. The composition according to claim 1, wherein the plasticiser consists of a mineral oil, of petroleum jelly and/or of a mixture of these compounds.

8. The composition according to claim 1, further comprising a tackifying resin selected from the group consisting of modified polyterpene or terpene resins, rosin resins, hydrocarbon resins, mixtures of cyclic, aromatic and aliphatic resins, and mixtures thereof.

9. The composition according to claim 1, further comprising particles of hydrocolloid and/or absorbent particles.

10. The composition according to claim 1, further comprising one or more active substance(s) selected from the group consisting of agents that promote skin healing, antibacterial agents, antiseptics, analgesics, local anaesthetics, and anti-inflammatory drugs.

11. The composition according to claim 1, wherein the composition has a permeability to water vapour (MVTR) that is greater than 250 g/m²/day.

12. An elastomer matrix obtained from a composition according to claim 1, by hot casting of said composition.

13. The elastomer matrix according to claim 12, wherein the elastomer matrix is in continuous or discontinuous form.

14. A device comprising an elastomer matrix according to claim 12.

15. The device according to claim 14, wherein the device is a dressing.

* * * * *